(12) United States Patent
Mak et al.

(10) Patent No.: US 6,290,978 B2
(45) Date of Patent: Sep. 18, 2001

(54) DERIVATIVES OF ARABINOGALACTAN AND COMPOSITIONS INCLUDING THE SAME

(75) Inventors: Chew-Hung Mak, Roseville, MN (US); Morton A. Westman, Oak Brook, IL (US); Michael Lynn Finney, Vadnais Heights; Richard Dale Lamb, Oakdale, both of MN (US)

(73) Assignee: Larex, Inc., White Bear Lake, MI (US)

( * ) Notice: Subject to any disclaimer, the term of this patent is extended or adjusted under 35 U.S.C. 154(b) by 0 days.

(21) Appl. No.: 09/727,035

(22) Filed: Nov. 30, 2000

Related U.S. Application Data (63) Continuation of application No. 09/300,150, filed on Apr. 27, 1999, now abandoned
(60) Provisional application No. 60/083,110, filed on Apr. 27, 1998.

(51) Int. Cl.[7] ............... A61K 7/00; A61K 7/06; A61K 7/46; A61K 47/00; C07H 1/00
(52) U.S. Cl. ............... 424/401; 106/31.01; 106/31.24; 106/31.36; 106/31.68; 106/38.23; 424/70.1; 424/70.2; 424/70.13; 424/70.6; 424/488; 426/531; 426/658; 512/1; 514/777; 514/844; 514/944; 514/945; 536/123.1
(58) Field of Search ................. 424/401, 70.1, 424/488, 70.2, 70.6, 70.13; 512/1; 514/777, 844, 944, 945; 536/123.1; 106/31.01, 31.24, 31.36, 31.68, 38.23; 426/531, 658

(56) References Cited

U.S. PATENT DOCUMENTS

| | | |
|---|---|---|
| 4,061,602 | 12/1977 | Oberstar et al. . |
| 4,254,105 | 3/1981 | Fukuda . |
| 4,472,297 | 9/1984 | Bolich, Jr. et al. . |
| 4,489,114 | 12/1984 | Bridgeford . |
| 4,764,365 | 8/1988 | Boothe et al. . |
| 4,818,751 | 4/1989 | Ibe . |
| 4,960,764 | 10/1990 | Figueroa, Jr. et al. . |
| 4,971,721 | 11/1990 | Takahashi et al. . |
| 4,985,459 | 1/1991 | Sunshine et al. . |
| 5,106,609 | 4/1992 | Bolich, Jr. et al. . |
| 5,116,969 | 5/1992 | Adams et al. . |
| 5,120,563 | 6/1992 | Mohlenkamp, Jr. et al. . |
| 5,136,093 | 8/1992 | Smith . |
| 5,478,576 | 12/1995 | Jung et al. . |
| 5,520,200 | 5/1996 | Sturla . |
| 5,567,685 | 10/1996 | Linden et al. . |
| 5,614,501 | 3/1997 | Richards . |
| 5,629,003 | 5/1997 | Horstmann et al. . |
| 5,756,098 | 5/1998 | Price et al. . |
| 5,863,527 | 1/1999 | Hitchins et al. . |
| 5,882,520 | 3/1999 | Richards et al. . |
| B1 5,116,969 | 4/1997 | Adams et al. . |

FOREIGN PATENT DOCUMENTS

| | | |
|---|---|---|
| 0 357 474 A1 | 3/1990 | (EP) . |
| 0 539 235 A2 | 4/1993 | (EP) . |
| 1 074 122 | 6/1967 | (GB) . |
| 2 260 333 | 4/1993 | (GB) . |
| 09310300 | 12/1997 | (JP) . |
| WO 94/13160 | 6/1994 | (WO) . |
| WO 98/11778 | 3/1998 | (WO) . |

OTHER PUBLICATIONS

A.W. Stout, "Larch Arabinogalactan", *Industrial Gums: Polysaccharides and Their Derivatives*, R.L. Whistler Ed., Academic Press, Inc., New York 307–310 (1959).

G.A. Towle et al., "Chemical Modification of Gums", *Industrial Gums: Polysaccharides and Their Derivatives*, Roy Whistler, Ed., Academic Press, Inc., New York, 53–67 (1993).

*Primary Examiner*—Shelley A. Dodson
(74) *Attorney, Agent, or Firm*—Mueting, Raasch & Gebhardt, P.A.

(57) ABSTRACT

Derivatized Arabinogalactan can be utilized in a variety of compositions to impart functionality without imparting negative rheological affects when the amount of the derivatized Arabinogalactan is increased in the composition. This is particularly important in the personal care industry, where it is desirable to have the flexibility to adjust the amount of derivatized Arabinogalactan depending upon the results it is desired to deliver to the user without negatively impacting the overall viscosity of the personal care composition.

14 Claims, 7 Drawing Sheets

DERIVATIVES OF ARABINOGALACTAN AND COMPOSITIONS INCLUDING THE SAME

This is a continuation of application Ser. No. 09/300,150, filed Apr. 27, 1999, which claims benefit of U.S. provisional patent application Ser. No. 60/083,110, both of which are incorporated herein by reference.

CROSS-RELATED APPLICATIONS

This application claims benefit from U.S. provisional patent application Ser. No. 60/083,110, filed Apr. 27, 1998.

FIELD OF THE INVENTION

The present invention relates to Arabinogalactan (AG) and in particular the present invention relates to Arabinogalactan derivatives and compositions including the same.

BACKGROUND OF THE INVENTION

Polymers, whether naturally occurring or synthetic, are generally included in personal care products, including hairsprays, shampoos, hair conditioners, skin creams, skin lotions, cosmetic products, antiperspirants, deodorants, shaving creams, topic drug compositions, sunscreen products, and the like, because of their rheological, holding, and film-forming properties.

Derivatives of naturally occurring polymers can provide chemical and physical properties that differ from the naturally occurring polymer. For example, cellulose and guar derivatives have been derived from chemical reaction with a variety of compounds, including ethylene or propylene oxide, sodium monochloroacetate, and quaternary reagents. Some of these derivatives produce substances that are solvent compatible, have greater clarity in solution as compared with the non-derivatized form, hydrate faster and have greater temperature stability. As a result these derivatives have improved use for liquid formulations. For example, cationic starch derivatives are important in the paper industry as wet-end additives where they act to increase dry strength. The chemical properties of the derivatives depend upon the base material being derivatized and upon the derivatizing reagent with which they are reacted. Derivatization with a cationic reagent can lend charge to a base polymer, providing the efficacy in the application that would otherwise be absent, e.g. cationic groups improve adhesion to polar substrates. Derivatization with a cationic reagent generally involves the use of either water-based or solvent-based, hydroxide catalyzed reactions, as described in the technical literature available from the suppliers of such reagents.

Quaternary ammonium (also referred to as "quaternized") derivatives of a number of commercially available polymers are known in the personal care industry to enhance substantivity (i.e., cling and resistance to removal upon rinsing with water) to anionic sites within hair or skin. Quaternized derivatives of cellulose, guar, and starch, for example, can be found in many personal care products.

The degree of substitution (D.S.), of derivatized polysaccharide polymers generally ranges from 0.05 to 0.25. The mode of reaction for polysaccharide polymers is typically through the hydroxyl groups associated with the sugar rings on the polysaccharide polymers. In one example, derivatization of polysaccharide polymers with ethylene or propylene oxide is catalyzed by a base hydroxide to yield polymer derivatives with a substitution level of one to fifty percent by weight of ethylene or propylene oxide. Ethylene or propylene oxide derivatized polysaccharide polymers have been used in the personal care area. In another example, double derivatives of starch, cellulose or guar can also be prepared, for example, using a quaternary amine.

In the industrial arena, hydroxypropyl cellulose and/or guar have been used as viscosifying agents for oil well drilling, oil well stimulation, fire fighting, textiles, paints and other applications. Derivatization of sugar containing polymers with sodium monochloroacetate (for example, to produce carboxy-methyl derivatives) yields anionic polymers that are also useful in industrial applications. For cxaiiiple thcsc derivatives function as wet strength additives in papermaking or in textile sizing. Hydroxypropyl methylcellulose has also been used in the cosmetic and personal care industries.

Typically, a derivatized polysaccharide polymer can also function as a viscosifying agent. Very low concentrations of any of the above derivatives can impart a high viscosity to a solution to which the derivatives are added. This is particularly true for solutions have some starting measurable viscosity. As a result of the added viscosity imparted by the derivatized polysaccharide polymer there is generally a low upper limit to the amount of derivatized polysaccharide polymer that can be added to these solutions. In addition, derivatized polysaccharide (including sugar and starch polymers) are typically salt and pH sensitive. Therefore, solutions containing these polymers are stable over limited salt concentration ranges and over narrow pH ranges. In addition, the derivatized polymers are often shear sensitive and generally non-Newtonian in that their apparent viscosity is lower with increased shear. When these polysaccharide polymers are added to an existing composition, the rheology of the composition typically increases and the solution also becomes shear sensitive. Adding functionality (i.e., substantivity, solvent compatability, pH compatability, or the like) through the addition of a derivatized polymer, therefore, typically has a potential negative rheological effect upon the entire composition.

SUMMARY OF THE INVENTION

There remains a need for polymer additives in the personal care and industrial markets that can impart functionality (that is, a functional benefit to the polymer such as, but not limited to, substantivity, solvent comparability, salt comparability, Newtonian rheology, non-pseudoplastic behavior, pH compatability, compatability with other additives, lowering irritation to skin, shear thinning, pourability, and the like) without imparting negative rheological affects to the composition. The addition of a polymer to a composition without increasing the viscosity of the product, inducing salt and pH incompatibilities, or causing the system to become shear sensitive or unstable with time, would be of benefit beyond polymers that are currently available. This is true whether the properties being sought are characteristic of the specific polymer being added, characteristic of hydrocolloids in general, or characteristic of the functional group derivatized with the polymer.

For example, in the hair care area, there is a continuing need for hair manageability and style retention. Many styling enhancing aids, including certain shampoo formulations, certain conditioning formulations, gels, mousses, and hair holding sprays, typically include a derivatized polymer, generally a quaternized polymer, or gum for coating the hair fibers and/or bonding them together. Some of these styling aids require additional application steps and time once styling is completed and, thus, can be inconvenient for the user. Some of these styling aids may deliver style enhancement in the form of a "rinse-off" product, such as a shampoo and/or conditioner. However, rinse-off products typically require styling agents that are substantive to the hair and are not readily removed during rinsing. For example, a conventional styling enhancing polymer used in rinse-off products resists removal as the result of water rinsing by bonding to anionic sites within the hair. Such materials may cause a build-up of a visible residue on the hair with repeated usage that can difficult to remove with conventional shampooing.

This invention provides polymer compositions that have little or no negative impact upon the personal care or industrial product properties while delivering the desired functional performance aspects.

As used herein, the term "Arabinogalactan," unless otherwise specified, includes naturally occurring or synthetic Arabinogalactan, portions of Arabinogalactan, such as degradation products, and chemically or biochemically modified Arabinogalactan or portions thereof which have been modified using methods available in the art.

As used herein, "ultrarefined Arabinogalactan" refers to Arabinogalactan, preferably isolated from a plant source such as trees of the genus Larix, with a purity greater than 95%.

As used herein, "derivatized" or a "derivative" of Arabinogalactan refers to a product of a chemical reaction between Arabinogalactan and a derivatizing reagent resulting in the attachment of at least one chemical moiety on the Arabinogalactan, preferably by attaching to a reactive site on the Arabinogalactan.

As used herein, the term "substantivity" describes a propensity of a compound to adhere to a given substrate and to resist removal by a typical water rinse procedure that generally follows application of a hair shampoo and/or conditioner.

One aspect of the present invention provides a composition including a derivatized Arabinogalactan. In one embodiment, the derivatized Arabinogalactan includes at least one cationic moiety. In another embodiment, the derivatized Arabinogalactan is selected from the group consisting of a single derivatized Arabinogalactan, a double derivatized Arabinogalactan, and a combination thereof. Preferably, the derivatized Arabinogalactan is selected from the group consisting of hydroxypropyl Arabinogalactan, carboxymethyl hydroxypropyl Arabinogalactan, quaternary ammonium Arabinogalactan, carboxymethyl Arabinogalactan, and a combination thereof.

The composition can be an ink, a paint or a coating. The composition can also be an adhesive. The composition can also be used in paper manufacturing. Additionally, the composition can be a personal care composition. The composition can also be a rheology control additive, an emulsification additive, a food additive, a formulation aid, a release agent or a processing aid. The composition can also be a food, or a pharmaceutical composition. The composition may also be a drilling fluid or a fracturing fluid.

In one embodiment, the personal care composition can be selected from the group consisting of a hair care composition, a skin care composition, a cosmetic, and a fragrance.

The derivatized Arabinogalactan is preferably derivatized with a derivatizing reagent that is present in an amount from about 1% to about 200% of a weight of Arabinogalactan.

Also provided is a method for making derivatized Arabinogalactan. The method preferably includes combining Arabinogalactan in a reaction solution with a derivatizing reagent selected from the group consisting of ethylene oxide, propylene oxide, a quaternary amine, sodium monochloroacetate, dimethylsulfate, methyl chloride, ketene, vinyl acetate, and a combination thereof to form a reaction product; and heating to a temperature of at least 37° C. for a time to produce a derivatized Arabinogalactan. Preferably, the reaction product is selected from the group consisting of quaternary ammonium Arabinogalactan, carboxymethylate Arabinogalactan, hydroxypropyl Arabinogalactan, carboxymethyl hydroxypropyl Arabinogalactan, and hydroxypropyl quaternary ammonium Arabinogalactan. Preferably, the reaction solution includes about 10% to about 20% by weight of Arabinogalactan. Preferably, the temperature is at least about 48° C. and is preferably less than about 82° C. The derivatizing reagent is preferably present in an amount of about 200% or less of a weight of Arabinogalactan.

Yet another aspect provides a derivatized Arabinogalactan produced by combining Arabinogalactan with a derivatizing reagent selected from the group consisting of ethylene oxide, propylene oxide, a quaternary amine, sodium monochloroacetate, dimethylsulfate, methyl chloride, ketene, vinyl acetate, and a combination thereof.

A further aspect of the present invention provides a composition comprising derivatized Arabinogalactan, the derivatized Arabinogalactan produced by combining Arabinogalactan with a derivatizing reagent selected from the group consisting of ethylene oxide, propylene oxide, a quaternary amine, sodium monochloroacetate, dimethylsulfate, methyl chloride, ketene, vinyl acetate, and a combination thereof.

Yet a further aspect of the present invention provides a personal care composition including a derivatized Arabinogalactan and a diluent. Preferably, the derivatized Arabinogalactan includes at least one cationic moeity. The derivatized Arabinogalactan can be selected from the group consisting of a single derivative of Arabinogalactan, a double derivative of Arabinogalactan, and a combination thereof.

Preferably, the derivatized Arabinogalactan is selected from the group consisting of hydroxypropyl Arabinogalactan, carboxymethyl hydroxypropyl Arabinogalactan, quaternary ammonium Arabinogalactan, carboxymethyl Arabinogalactan, and a combination thereof. The derivatized Arabinogalactan is preferably quaternized ammonium Arabinogalactan.

A personal care composition of the present invention preferably includes from about 0.05% to about 25% by weight derivatized Arabinogalactan. The personal care composition can further include at least one additive selected from the group consisting of a surfactant, an emulsifier, a foam modifier, a humectant, a moisturizer, a thickener, an emollient, a conditioning agent, a specialized functional ingredient, a preservative, an antioxidant, a chelator, a sequestrant, and an aesthetic component. The personal care composition can further include a specialized active ingredient in an amount of about 0.01% to about 10% by weight of the composition.

In one embodiment, the personal care composition is a hair care composition. Preferably, the hair care composition can be selected from the group consisting of a shampoo, a conditioner, a hair tonic, a setting lotion, a setting gel, a mousse, a hair spray, a permanent hair color treatment, a non-permanent hair color treatment, a permanent wave treatment, a hair relaxer, and a pommade.

DETAILED DESCRIPTION OF THE INVENTION

Arabinogalactan is a water-soluble polysaccharide that can be isolated from species of the genus Larix. Arabinogalaetan can constitute up to 35% of the total heartwood of some species (Stout, "Larch Arabinogalactan" in Industrial Gums, R. L. Whistler Ed., Academic Press, New York, pp. 307–310, 1959). Arabinogalactan is highly soluble and can be obtained at 95% purity from larch chips. In a preferred embodiment, ultrarefined Arabinogalactan (i.e., highly purified) is used in this invention. One method for the preparation of ultrarefined Arabinogalactan is disclosed in U.S. Pat. No. 5,116,969 (Adams et al.). Ultra-refined Arabinogalactan of greater than 95%, or optionally, greater than 99.9% purity is preferably used. A suitable example is commercially available under the trade designations LAREX UF and LARACARE A200, both from Larex, Inc., St. Paul, Minn. Ultrarefined Arabinogalactan advantageously makes little or no contribution to the osmolality of aqueous solutions in which it is a solute. Ultrarefined Arabinogalactan is highly stable, non-toxic and highly water soluble. In another embodiment, Arabinogalactan material is used as produced and described in U.S. Pat. No. 5,756,098 (Price et al.).

A variety of Arabinogalactans can be used in this invention. In one embodiment, the molecular weight of the Arabinogalactan ranges from about 6,000 Daltons to about 2,500,000 Daltons. In another embodiment, the molecular weight of the Arabinogalactan used is between about 6,000 Daltons to about 300,000 Daltons and in another embodiment between about 10,000 Daltons to about 30,000 Daltons as assessed by size exclusion liquid chromatography using Pullulan reference standards available from Millipore Corporation (Milford, Mass.).

Figure 1:
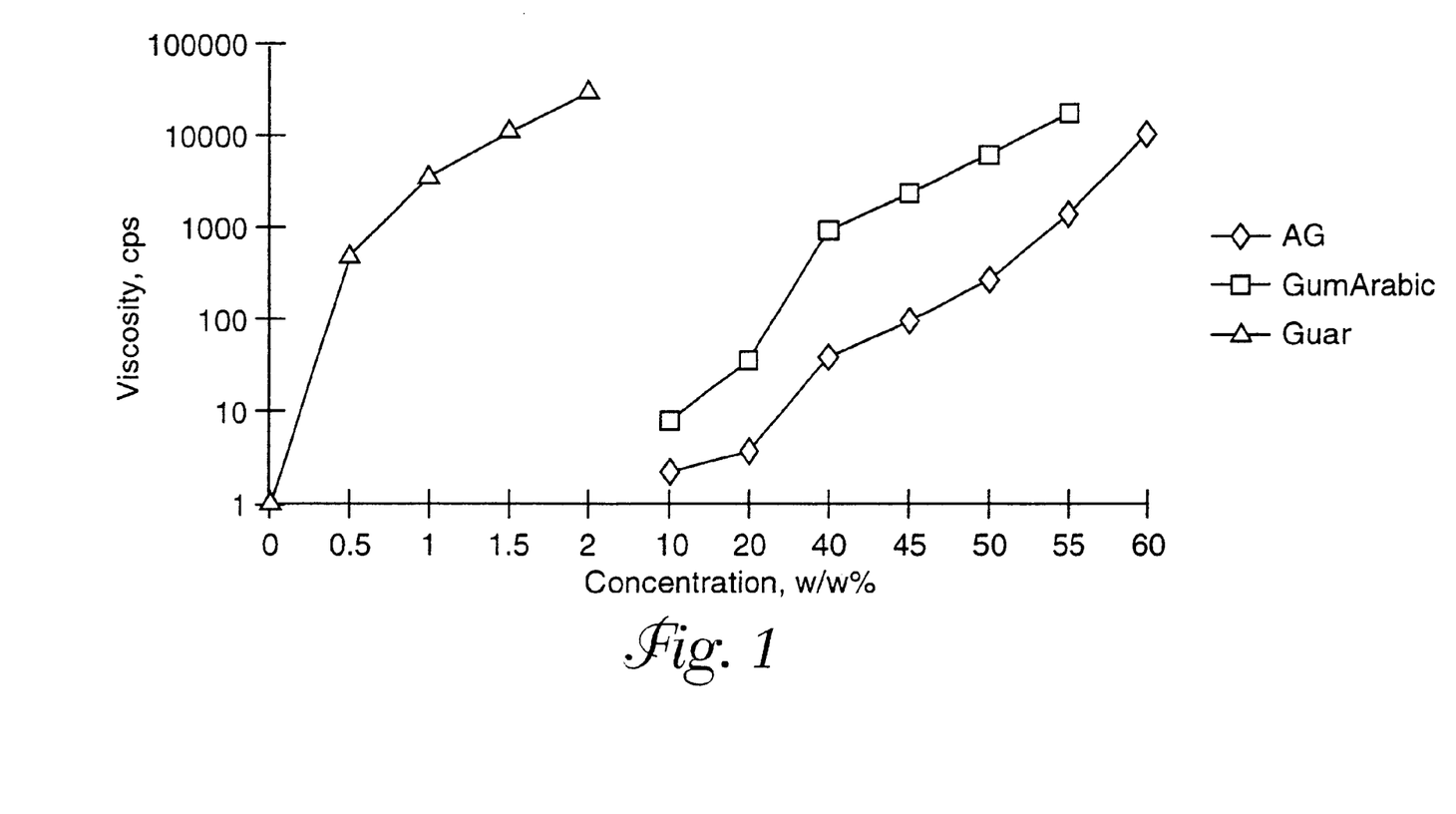
FIG. 1 is a viscosity profile for Arabinogalactan as compared to gum arabic and guar.

Arabinogalactan has a number of benefits as compared with other polysaccharide polymers. Arabinogalactan is water-soluble, occurs naturally with a narrow molecular weight distribution as compared to, for example, gum arabic and guar. As shown in FIG. 1, a concentration of Arabinogalactan of about 55 w/w % results in a viscosity of a about 1000 cps, while a viscosity of about 1000 cps is achieved with concentrations of about 40 w/w % and about 0.75 w/w % for guar and gum arabic, respectively. While not wishing to be bound by any particular theory, it is believed that because Arabinogalactan is highly branched it is not subject to viscosity problems, as compared to other polymers.

Figure 2:
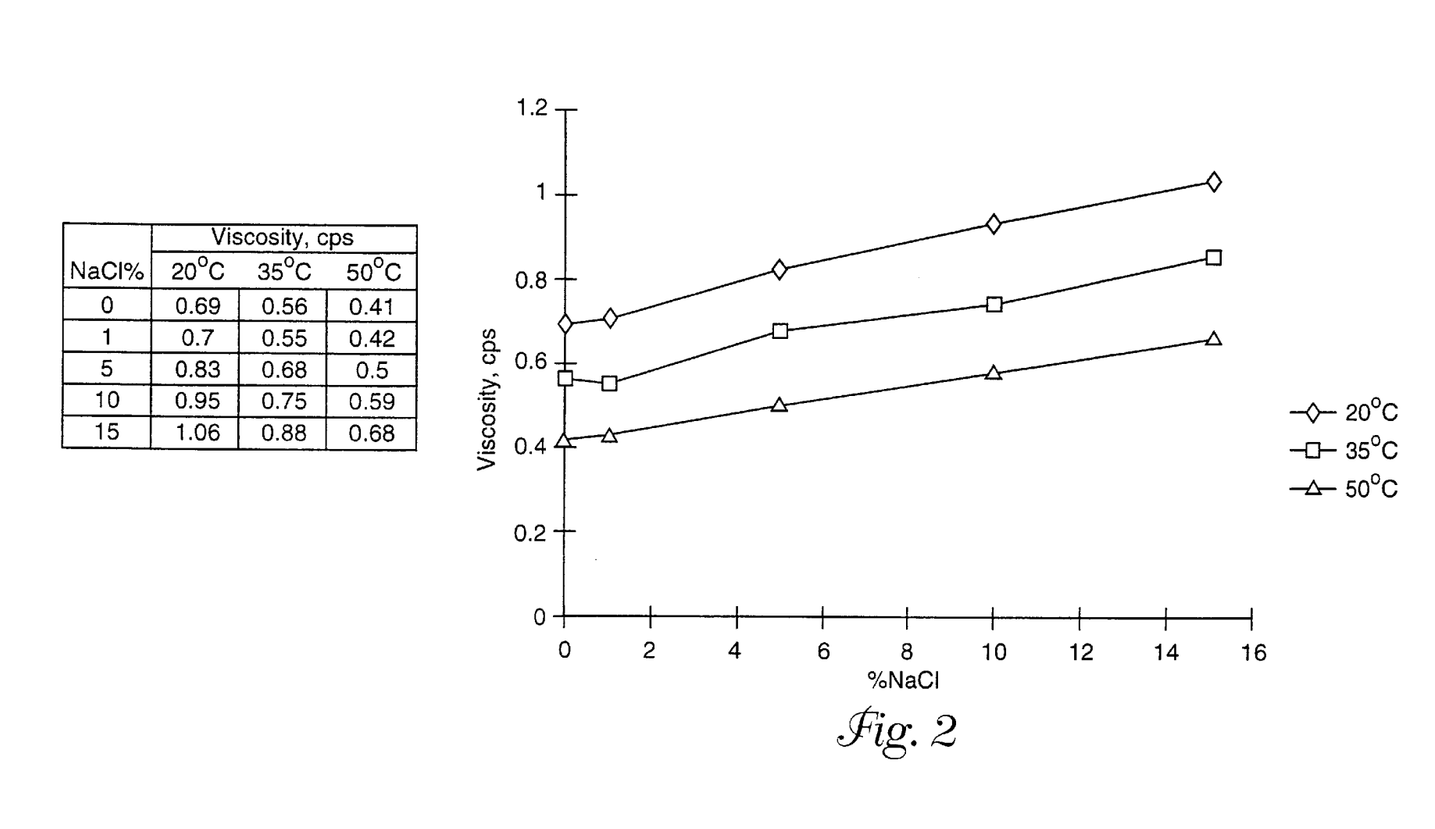
FIG. 2 illustrates one example of the salt compatibility of Arabinogalactan at three temperatures and salt concentrations ranging from 0% to 16% NaCl.
Figure 3:
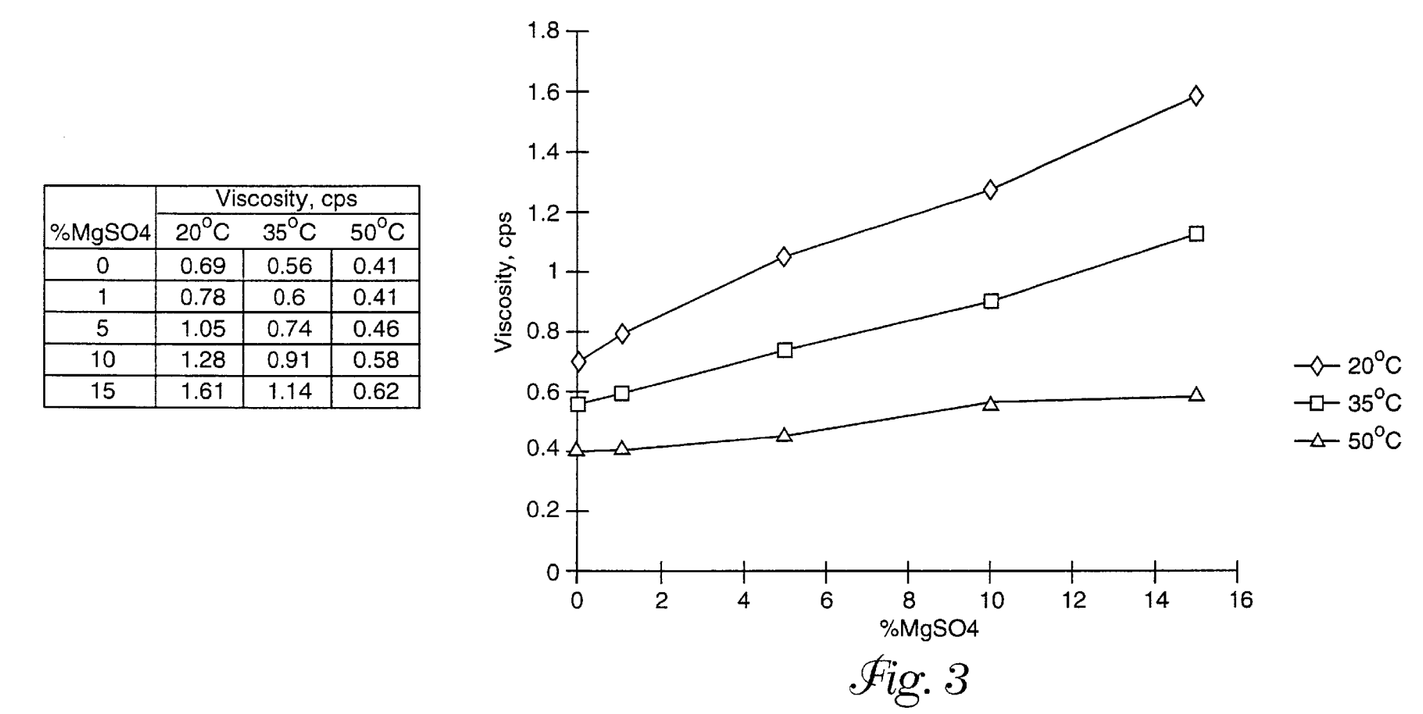
FIG. 3 illustrates another example of the salt compatibility of a 10% Arabinogalactan solution at three temperatures from 0% to 16% $MgSO_4$.

Arabinogalactan salt compatibility is unusually good. Unlike the phenomenon observed with most hydrocolloids, increasing salt concentration has a very little impact on the apparent viscosity of an aqueous 10% Arabinogalactan solution. Referring to FIGS. 2 and 3, viscosity measurements were taken for a 10% Arabinogalactan solution containing sodium chloride or magnesium sulfate, respectively, from zero to fifteen percent by weight. Viscosity measurements were taken using a Brookfield Viscometer at three different temperatures. As shown in FIG. 2, there is a negligible increase in viscosity of from about 0.7 cps to about 1.05 cps in the case of NaCl at 20° C. A similar effect was observed in the case of $MgSO_4$ at 20° C., where there was a negligible increase from about 0.7 cps to about 1.6 cps. At 50° C., a negligible increase is again substantially linear from about 0.4 cps to about 0.7 cps for NaCl and to about 0.6 cps for $MgSO_4$.

Figure 4:
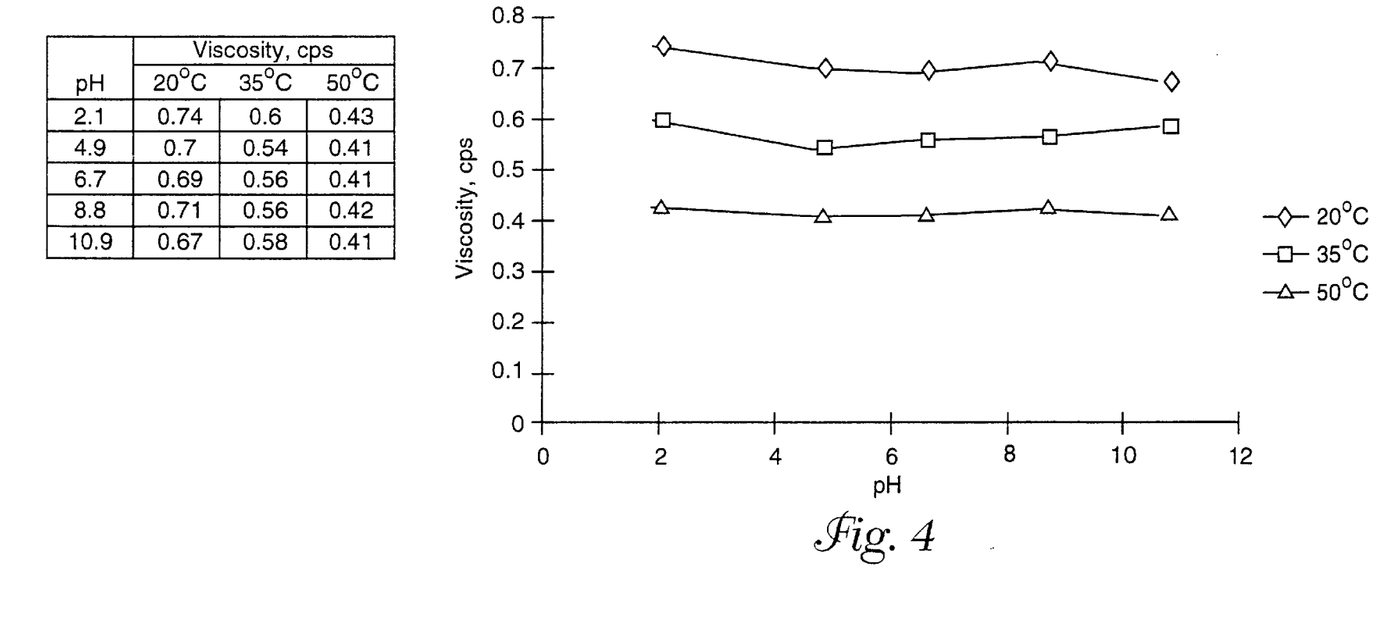
FIG. 4 illustrates the viscosity of a 10% Arabinogalactan solution measured from a pH of about 2 to about 11.

Also, unlike other polysaccharide polymers, the response of a 10% Arabinogalactan solution with a pH increase from 2 to 11 results in a very small change in apparent viscosity, decreasing from about 0.75 cps at pH 2 to about 0.65 cps at pH 11 (at 20° C.), as shown in FIG. 4. At 50° C., the relationship shows even less change, staying around 0.4 cps as the pH values increase from 2 to 11. In contrast, many conventional polysaccharide polymers are fairly sensitive to pH changes, which results in a substantial change in viscosity.

Figure 5:
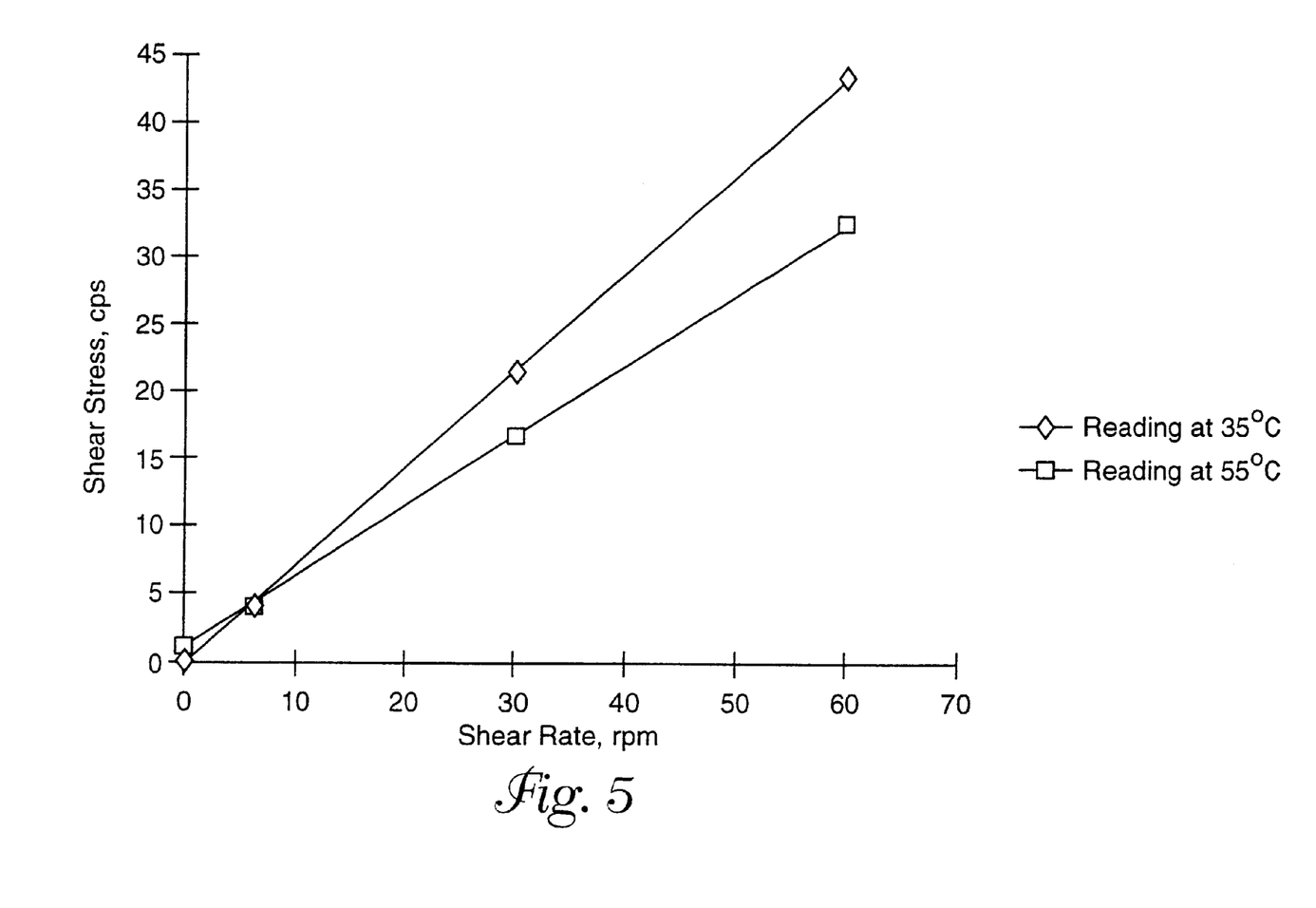
FIG. 5 illustrates the shear stress versus shear rate for a 25% Arabinogalactan solution at two temperatures.
Figure 6:
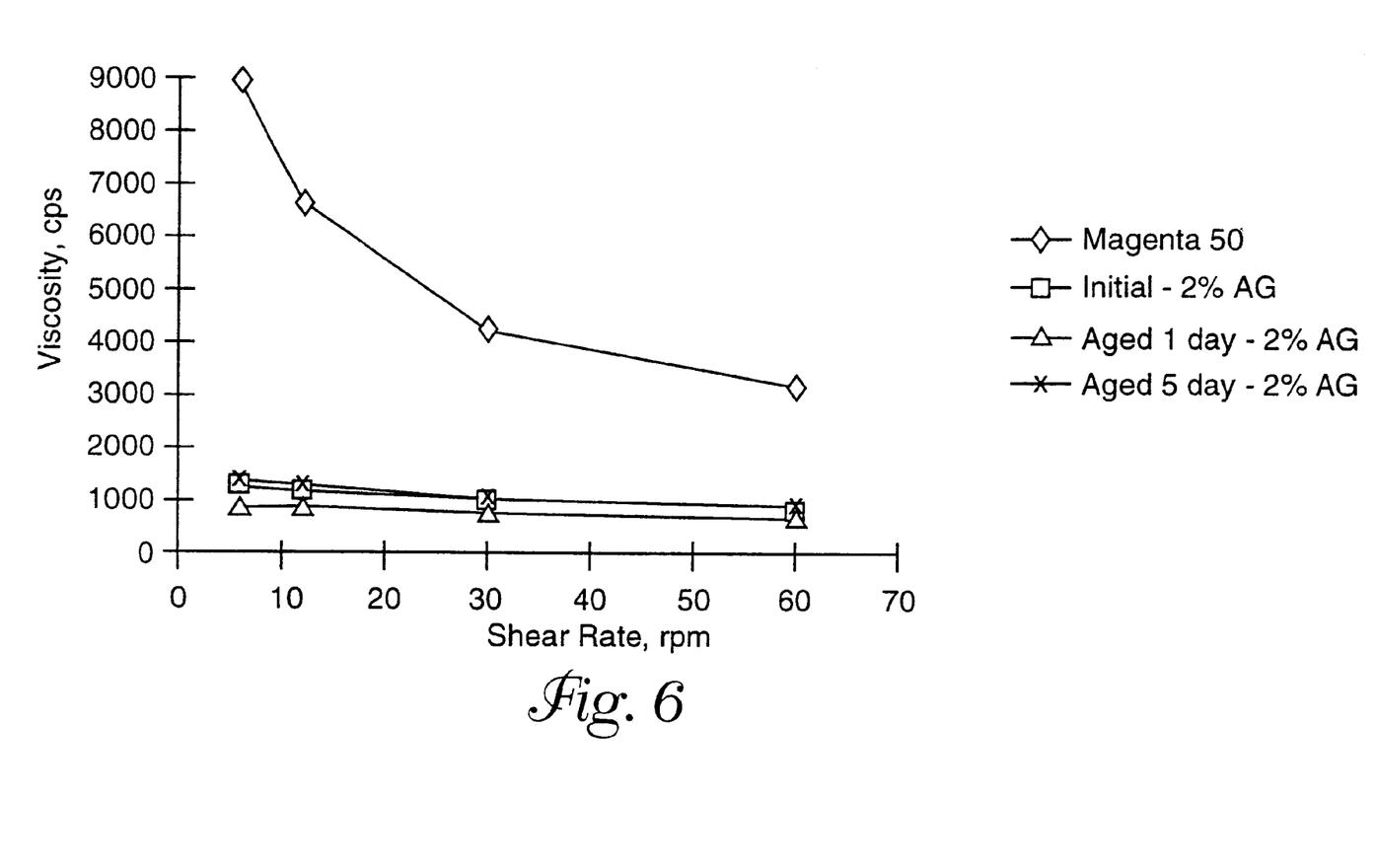
FIG. 6 illustrates the shear stress versus shear rate in a water-based ink system with and without Arabinogalactan.

Arabinogalactan solutions are Newtonian solutions (i.e., solutions in which the relationship between shear stress and shear rate is substantially linear). For a 25% Arabinogalactan solution, increasing shear rate from zero to sixty revolutions per minute (rpm) on a Brookfield CP Viscometer increased shear stress linearly from zero to forty five cps (at 35° C.), as shown in FIG. 5. This characteristic of Arabinogalactan transfers from a simple solution of the material to many complex systems containing Arabinogalactan. For example, a water-based ink system, such as magenta ink without Arabinogalactan, exhibited a decrease in viscosity from about 9000 cps to about 3000 cps as the shear rate increased from five and sixty rpm, as illustrated in FIG. 6. The same ink system with 2% Arabinogalactan had a flat viscosity profile of about 1000 cps as the shear rate increased between the same two rpm values.

Arabinogalactan also stabilizes emulsions. It has been observed in photomicrographs of oil-in-water systems containing Arabinogalactan, the oil-in-water emulsion can be characterized as having smaller and more uniform oil droplets. The ability of Arabinogalactan to produce smaller, more uniform droplets tends to enhance the stability of Arabinogalactan-containing systems over time and is generally known to enhance performance properties. These emulsions have application in cosmetic, personal care, food and industrial applications.

A variety of Arabinogalactan derivatives can be prepared using methods known in the art, such as methods available for derivatizing polysaccharides including cellulose, guar, gum arabic, and the like (Gordon Towle, Chemical Modification of Gums, Industrial Gums, Roy Whistler, Ed., Academic Press, New York, 1993, pp 53–67). Typically, reactive sites on Arabinogalactan include primary and secondary hydroxyl groups that occur naturally as part of the sugar ring structure. Alternatively, reactive hydroxyl groups can be added as a result of a chemical modification. Arabinogalactan can be chemically modified prior to derivatization or simultaneously or sequentially as part of the derivatization reaction.

In general, the derivatized Arabinogalactan is prepared by dissolving or suspending the Arabinogalactan in a water or solvent phase and combined with a derivatizing reagent. The reaction can be catalyzed by a base hydroxide (typically KOH or NaOH) and can be either exothermic or endothermic, depending on the reagent used. The resulting derivatives can optionally be further refined and/or purified to eliminate unwanted salts, impurities and/or reaction by-products.

Derivatized Arabinogalactan can be prepared by reacting Arabliogalactan with one or more of the following derivatizing reagents: ethylene oxide, propylene oxide, quaternary amines, lauryl dimethyl quat, sodium monochloroacetate, dimethyl sulfate, methyl chloride, ketene, and vinyl acetate. The derivatized Arabinogalactan can be tested for use in particular compositions and for their composition altering properties such as, but not limited to, shear stress, viscosity, pH, salt sensitivity, and the like. The characteristics of the derivatized Arabinogalactan will depend on the type and extent of the degree of substitution. As will be understood in the art, the degree of substitution can be controlled by limiting the amount of reagent or catalyst in contact with the polysaccharide.

In addition to derivatization reactions which result in chemical modification by attachment of the reagent molecule to the polysaccharide, other derivatization reactions exist that do not significantly chemically modify the sugar structure but rather change the apparent viscosity of the resulting solutions, for example, by either depolymerizing the polysaccharide or by complexing the material in solution or in use (termed depolymerized Arabinogalactan or complexed Arabinogalactan). These reactions can be carried out by oxidizing the polysaccharide, for example, using hydrogen peroxide in the presence of a base, or by inclusion of a material such as a transition metal or borate ion, which complexes the structure through hydroxyl crosslinking between polymer chains. This technology is discussed in the art (Whistler, supra).

Quaternary ammonium Arabinogalactan derivatives can be prepared in an aqueous solution through the reaction of a quaternary reagent with Arabinogalactan, preferably in the presence of a base. Suitable quaternary reagents include 3-chloro-2-hydroxypropyl trimethylammonium chloride, and those commercially available under the trade designations DOW QUAT 188, from Dow Corporation, Freeport, Tex., and DEGUSSA QUAB 188, from Degussa Corp., Ridgefield Park, N.J. One preferred base is sodium hydroxide. For example, a solution of Arabinogalactan, from about 10% to about 70% solids, is mixed with about 65% active quaternary reagent (about 10% to about 200% by weight of Arabinogalactan) and a concentrated sodium hydroxide solution (about 20% to about 100% by weight of Arabinogalactan) at room temperature. The reaction mixture is slowly heated over a period of one hour to about 120° F., and held at this temperature for about one hour, then cooled and either spray or drum dried. The resulting solid material can be used in the industrial market, such as for paper applications, including, but not limited to, inks, adhesives, and the like, or extensively washed with a solvent, such as methanol or isopropanol to remove contaminants where the derivates can be used in the personal care industry.

Alternatively, quaternary ammonium Arabinogalactan can be prepared in solvent reactions. In one example, about 10% to about 70% Arabinogalactan solids as a slurry in methanol, ethanol, IPA (isopropyl alcohol) or other appropriate solvent or aqueous solvent solution, in which Arabinogalactan is only partially soluble or totally insoluble, is prepared. The quaternary reagent is added to the slurry or solution, either in concert with, before or after the addition of an hydroxide base such as sodium hydroxide or potassium hydroxide. The reaction mass is heated gradually to about 120° F. (about 48.9° C.) over a period of one hour, held at that temperature for about one hour, then cooled and discharged. The solid material is separated from the solvent using existing technology in the art, as for example with a solid bowl centrifuge, and then cake oven dried, ground in a pin or hammer mill and sifted to the desired mesh. Alternately, the solid material can be extensively washed in solvent to remove reaction by-products and other contaminants and then dried.

Production of a quaternary ammonium Arabinogalactan compound is primarily targeted at, but not limited to, the personal care industry. Other potential compounds with Arabinogalactan for use in the personal care industry include stearyl or lauryl derivatives. These derivatives can be produced using the above chemical routes or modifications using quaternary ammonium reagents.

Double derivatives of Arabinogalactan, i.e., Arabinogalactan including two chemical moieties, can be prepared. For example, a double derivative of Arabinogalactan for inclusion in a personal care composition, can include Arabinogalactan having either a quaternary, lauryl or stearyl group and either a hydroxypropyl or hydroxyethyl group. Substitution levels can be about 1% to about 100% by weight of Arabinogalactan for each reacted derivatizing reagent, but preferred in the range of about 1% to about 50% and most preferred in the range of about 1% to about 20% by weight of Arabinogalactan.

Single derivatives of Arabinogalactan with ethylene or propylene oxide can be produced in pressurized reaction vessels either in an aqueous or a solvent phase. As above, about 10% to about 70% solids solution or slurry is prepared and the reagents are added (about 10% to about 200% by weight of Arabinogalactan) together with, before or after the addition of the catalyzing base (typically about 50% base solution at about 10% to about 20% by weight of polysaccharide). The reaction mass is heated to a minimum of about 120° F. (about 48° C.), after which the exothermic reaction is cooled and temperatures below about 180° F. (about 82° C.) are maintained. The reaction is carried out in an inert environment, such as a nitrogen atmosphere with or without the addition of pressure. The resulting solution or solids are treated as above with the quaternary reaction products. The substitution levels of the resulting compounds can be in the range of about 1% to about 200% by weight of Arabinogalactan.

Carboxymethyl Arabinogalactans are produced by reacting Arabinogalactan, as above, with sodium monochloroacetate. This reaction is typically endothermic and must be heated from about 150° F. (about 66° C.) to about 170° F. (about 77° C.) to achieve the desired reaction efficiencies and substitution levels. Derivatizing reagent and base levels parallel that of the quaternary amine reactions, along with overall substitution levels.

Other derivatizing reagents as previously mentioned can be reacted with Arabinogalactan using methods similar to or identical to the above methods for quaternary amines, ethylene or propylene oxides or sodium monochloroacetate.

Derivativatized Arabinogalactan of this invention can be used for the same purposes as underivatized Arabinogalactan or for the same uses as other polysaccharides, natural, synthetic or derivatized, with the advantages that: (1) the derivatization adds functionality, including the addition of a charged group, to the base Arabinogalactan; (2) the derivatization can provide solubility, for example, ethylene oxide derivatized Arabinogalactan as compared with the non-derivatized Arabinogalactan polymer; (3) the derivatization can provide enhanced functionality as a result of higher polymer solids loading occurring because of the low viscosity of unmodified Arabinogalactan; and/or (4) the derivative combines the benefits of Arabinogalactan (as compared to cellulose for example) including reduced irritation and improved mildness, with the benefits of the derivative, such as for example solvent compatibility.

As compared with other polymer derivatives, such as cationic guar, a derivatized Arabinogalactan including at least one cationic group, preferably a quaternary ammonium group, exhibits reduced viscosity (an important characteristic for personal care formulations) as compared with other polysaccharide polymers at the same polymer amounts. Because derivatized Arabinogalactan in accordance with the present invention preferably includes at least one cationic group, single cationic derivatives or double derivatives of Arabinogalactan having at least one cationic group are preferred. Preferably, the cationic group is a quaternized hydroxypropyl group. A suitable derivative Arabinogalactan is commercially available under the trade designation of LARACARE C300, from Larex, Inc., St. Paul, Minn. Single cationic derivatives or double derivatives can be used in systems where a positively charged derivative tends to act as a surfactant or to bind charged moieties or where increased aqueous and/or solvent compatibility is preferred.

Derivatized Arabinogalactan according to this invention can be used in a variety of compositions. One particularly useful area is in personal care compositions. Arabinogalactan derivatives having at least one cationic moiety can be used in personal care compositions to impart substantivity to the hair or skin, reduced skin or scalp irritation, improve emulsification properties, improve temperature stability, and the like. Suitable derivatized Arabinogalactans can include one, two, three, four, or more, chemical moieties, so long as at least one moiety is cationic.

Examples of personal care compositions include, but are not limited to skin care products, hair care products, cosmetics (including pigmented compositions), and fragrance compositions, to name a few. Skin care products can include soap (e.g., in solid, liquid, or gel form), creams, lotions, deodorants and antiperspirants (e.g., in solid, liquid, gel, or spray form), dry skin care treatments and products, products that improve the look and feel of the skin, such as skin tighteners, skin cleansers, skin cell exfoliants, skin ultraviolet absorption protection products including sun screens, tanning lotions, anti-aging skin preparations including reduced wrinkle skin preparations, and the like. Hair care products can include shampoo, hair tonics, settings, gels, hair sprays, conditioners and permanent or non-permanent hair color treatments, hair curling and straightening solutions, for example. Cosmetics can include such pigmented and non-pigmented products, such as lip sticks, lip protectants, mascara, and facial cosmetics, such as rouge, blush, eye shadows, foundation liquids and creams, face powders, and the like. Fragrance compositions can be in any conventional form, such as solid, liquid, lotion, gel, powder, to name a few.

A derivatized Arabinogalactan in accordance with the present invention can be used in a variety of other industrial applications such as dry strength additives for paper, retention aids, flocculants, fabric softeners, antistatic agents, water treatment chemical additives, surfactants, antimicrobial agents, corrosion inhibitors, crude oil demulsifiers, textile sizing, coatings, electroplating, and the like.

Derivatives of Arabinogalactan with derivatizing reagents such as ethylene or propylene oxide can be used in systems where the use of a nonionic Arabinogalactan derivative promotes increased or decreased solvent compatibility, increased hydrogen bonding, cross-linking or the formation of complexed gels, increased temperature stability, and the like. Such applications include, but are not limited to, those listed above in the personal care or cosmetic industries where the charge or polarity associated with the double derivative involving a cationic charge are not required, for example, low VOC hair sprays; industrial applications such as use as an emulsifier or emulsification aid, use in solvent adhesives, coatings and paints, in films, as a binder in paper or cellulose substrates or equivalent composite materials, in textile printing, sizing and dyeing, in oil or gas drilling or recovery, as a general processing aid, in paper formation to improve drainage and retention, as an explosives stabilizer or water blocking agent, in building trade materials for water binding and stabilization, in high salts applications such as brine waters and wash waters from mineral and oil applications, and the like.

Derivatives of Arabinogalactan with derivatizing reagents such as sodium monochloroacetate yield anionic Arabinogalactan derivatives with utility in detergents, soaps, textile sizing, coating paper and paper board, oil and gas drilling, inks, paints, and use as a suspending agent and emulsifier. These uses result from the negative charge and/or polarity that is associated with the carboxy Arabinogalactan derivative.

Derivatives of Arabinogalactan can also be included in a food (including human and/or animal feed), a pharmaceutical composition (including a nutraceutical/dietary supplement), and the like.

A "food" is meant to refer to any substance or mixture that, when ingested by a human or an animal, provides energy and contributes to the maintenance of vital processes of the human or animal. Foods can include any number of ingredients such as proteins, fats, carbohydrates, vitamins, minerals, and food additives (e.g., flavorings, spices, preservatives, dyes, to name a few). Foods can be delivered in a variety of formns, such as a solid or a liquid (i.e., as a beverage). It is contemplated that derivatized Arabinogalactan can be included in a human food, typically in pre-prepared food stuffs that can be packaged meals, snack bars, snack chips, nutritional drinks and shakes, and the like. It is further contemplated that derivatized Arabinogalactan can be included in animal feeds formulated for agricultural animals (e.g., as bovine feed, equine feed, swine feed, poultry feed, and the like). Further, derivatized Arabinogalactan can be included in animal feeds formulated for domestic animals, such as dogs, cats, hamsters, ferrets, and the like.

A "pharmaceutical" is meant to refer to a composition that can be administered to supplement a diet and/or prevent, cure, or treat a condition or disease of a human and/or an animal. A dietary supplement (or nutraceutical) typically contains a vitamin, a mineral, a herb or other botanical material, an amino acid, and a combination thereof and is intended to increase the total dietary intake of the human/animal to which it is administered. A pharmaceutical composition can include a carrier, preferably an edible carrier if it is to be administered orally. In particular, for the purposes of oral administration, the pharmaceutical composition can be incorporated with excipients and used in the form tablets, troches, capsules, suppositories, and the like. If the composition is in the form of a tablet, pill, capsule, troche, and the like, it can contain any of the following ingredients (or compounds of a similar nature): a binder (such as microcrystalline cellulose, gum tragacanth, gelatin, and the like), an excipient (such as starch, lactose, and the like), a disintegrating agent such as alginic acid, corn starch, and the like), a lubricant (e.g., magnesium stearate), a glidant (e.g., colloidal silicon dioxide), a sweetening agent (e.g., sucrose, saccharin, and the like), a flavoring agent (e.g., peppermint, methyl salicylate, orange flavoring, and the like), dyes, as well as others known to those skilled in the art. The pharmaceutical composition can be administered as a component of an elixir, suspension, syrup, wafer, chewing gum, and the like.

Personal Care Compositions

As mentioned above, a derivatized Arabinogalactan can be included in a personal care composition in accordance with the present invention, including skin care compositions, hair care compositions, cosmetics (including pigmented compositions), fragrance compositions, and the like. Suitable derivatized Arabinogalactans preferably include at least one cationic moiety and can be selected from the group of a single derivative or a double derivative of Arabinogalactan. Preferably, the derivatized Arabinogalactan is a single cationic derivative of Arabinogalacatan or double derivative of Arabinogalactan containing at least one cationic group. Suitable derivatized Arabinogalactans can be selected from the group consisting of hydroxypropyl Arabinogalactan, carboxymethyl hydroxypropyl Arabinogalactan, quaternary ammonium Arabinogalactan, carboxymethyl Arabinogalactan, and a combination thereof. While not wishing to be bound by any particular theory, it is believed that a single cationic derivatives or a double derivative of Arabinogalactan including at least one cationic moiety are used in systems where a positively charged derivative tends to be attracted to and, hence, adhere to anionic sites on a given substrate (e.g., on the hair or skin), or where modified aqueous and/or solvent compatibility is preferred. Thus, single cationic derivatives or double derivatives including at least one cationic moiety can be used in the cosmetic industry to improve the condition of skin and hair and for other applications which such compositions of the present invention can be employed. In addition, derivatized Arabinogalactan including at least one cationic moiety can improve emulsification properties, temperature stability, and other properties of such compositions of the present invention. A more preferred derivative is hydroxypropyl-quaternary amine Arabinogalactan.

Advantageously and unexpectedly, the amount of a derivatized Arabinogalactan in accordance with the present invention included in a personal care composition can be adjusted depending upon the results it is desired to deliver to the user without adversely affecting the overall viscosity of the composition. This is contrary to what has been observed or would be expected with other conventional derivatized polymers, such as derivatized guar, derivatized cellulose, derivatized acrylates, and the like, where increasing the amount of the conventional derivatized polymer typically leads to an increase in viscosity.

A personal care composition in accordance with the present invention preferably includes about 0.05% to about 25%, more preferably about 0.1% to about 15%, and even more preferably about 0.1% to about 10% by weight derivatized Arabinogalactan.

In addition to a derivatized Arabinogalactan, a personal care composition in accordance with the present invention preferably includes a diluent. Optionally, a personal care composition in accordance with the present invention can include at least one additive such as a surfactant, an emulsifier, a foam modifier, a humectant, a moisturizer, a thickener, an emollient, a conditioning agent, a specialized functional ingredient (e.g., an antibacterial, an antidandruff agent, an antiacne agent, a pharmaceutical agent, and the like), a preservative, an antioxidant, a chelator, a sequestrant, an opacifier, a colorant, a fragrance, and any other aesthetic component.

Diluent

Personal care compositions in accordance with the present invention can be delivered to the user in a variety of forms, such as a solid, a liquid solution, an emulsion, a mousse, a gel, a lotion, a cream, an ointment, a tonic, a spray, an aerosol, a gel stick, to name a few. Thus, a personal care composition in accordance with the present invention preferably includes a diluent that is compatible with the desired form of delivery and the desired application. Preferably, a diluent included in a personal care composition in accordance with the present invention can be selected from the group consisting of water, an organic solvent, and a combination thereof. In addition to water, suitable organic solvents include alcohols, mineral oil, a silicon-containing solvent, a hydrophobic solvent, and a combination thereof. Preferably, a personal care composition in accordance with the present invention includes from about 1% to about 99.75%, more preferably from about 25% to about 99%, and even more preferably from about 50% to about 90% by weight of a diluent.

If included, a hydrophobic solvent is preferably a hydrophobic hydrocarbon solvent. A hydrocarbon is classified as a compound including an aliphatic group, cyclic group, or a combination of aliphatic and cyclic groups (e.g., alkyl and aryl groups). In the context of the present invention, the term "aliphatic group" means a saturated or unsaturated linear or branched hydrocarbon group. This term is used to encompass alkyl, alkenyl, and alkynyl groups, for example. The term "alkyl group" means a saturated linear or branched hydrocarbon group, including, for example, methyl, ethyl, isopropyl, t-butyl, heptyl, dodecyl, octadecyl, amyl, 2-ethylhexyl, and the like. The term "alkenyl group" means an unsaturated linear or branched hydrocarbon group with one or more carbon-carbon double bonds, such as a vinyl group. The term "alkynyl group" means an unsaturated linear or branched hydrocarbon group with one or more triple bonds. The term "cyclic group" means a closed ring hydrocarbon group that is classified as an alicyclic group, aromatic group, or heterocyclic group. The term "alicyclic group" means a cyclic hydrocarbon group having properties resembling those of aliphatic groups. The term "aromatic group" or "aryl group" means a mono- or polynuclear aromatic hydrocarbon group. The term "heterocyclic group" means a closed ring hydrocarbon in which one or more of the atoms in the ring is an element other than carbon (e.g., nitrogen, oxygen, sulfur, etc.).

Preferred hydrophobic hydrocarbon solvents include branched chain hydrocarbons, more preferably saturated branched chain hydrocarbons. Preferably, preferred saturated branched hydrocarbons have from about 7 to about 14, more preferably from about 10 to about 13, and even more preferably from about 11 to about 12 carbon atoms. Suitable examples include isoparaffins, such as those commercially available under the trade designation of ISOPAR E, ISOPAR H, ISOPAR K, and ISOPAR L, all available from Exxon Chemical Co., Houston, Tex., isodecane, such as that commercially available under the trade designation PERMETHYL, from Presperse, Inc., S. Plainfield, N.J.; isoundecane; and a combination thereof.

Preferred silicone-containing solvents useful in the present invention include siloxanes, such as phenyl pentamethyl disiloxane, phenylethylpentamethyl disiloxane, hexamethyl disiloxane, emthoxy propylemethyl cyclotetrasiloxane, chloropropyl pentamethyl disiloxane, hydroxypropyl pentamethyl disiloxane, octamethyl cyclotetrasiloxane, decamethyl cylcopentasiloxane, and a combination thereof.

A suitable diluent can be in a variety of forms for use in the present invention, such as a water-in-oil emulsion, an oil-in-water emulsion, a water-in-oil-in-water emulsion (such as that described in U.S. Pat. No. 4,254,105 to Fukuda), an oil-in-water-in-silicone emulsion (such as that described in U.S. Pat. No. 4,960,764 to Figueroa, et al.), to name a few. Such emulsions can be of a variety of viscosities, typically falling within a range of about 200 cps to about 200,000 cps. These emulsions can be delivered in a variety of forms, such as a lotion or cream, a spray (aerosol/atomized), a mousse, a gel, and the like.

For example, preferred cosmetically acceptable diluents include liquid solutions, hydro-alcoholic systems, water-in-oil emulsions, and oil-in-water emulsions. If the diluent is a hydro-alcoholic system, the diluent preferably includes about 1% to about 60%, more preferably about 5% to about 20% of an alcohol, and preferably about 40% to about 99%, more preferably about 50% to about 80% water. Preferably, the alcohol is selected from the group consisting of ethanol, isopropanol, and a combination thereof. When the diluent is an oil-in-water emulsion, it can include any excipient ingredient as is known in the art for preparing these emulsions.

A suitable diluent, and other additives, included in a personal care composition in accordance with the present invention can be chosen by one skilled in the art, depending upon the desired personal care end-product, form of delivery and any other desired characteristics (e.g., providing UV protection, color, fragrance, dandruff treatment, acne treatment, etc.), as will be described below.

Preferably, a personal care composition in accordance with the present invention has a pH of about 3.0 to about 10.5. One with skill in the art will appreciate that the pH of a personal care composition in accordance with the present invention will depend upon the results it is desired to deliver to the user. For example, a hair condition typically has a pH in the range from about 3.0 to about 5.0, a shampoo typically has a pH in the range from about 5.0 to about 9.0, while a hair dye typically has a pH in the range from about 9.0 to about 10.5. The pH can be adjusted to the desired level using an acid and/or alkaline material. For example, citric acid or water soluble amine compounds, such as triethanolamine, can be used to adjust the pH to the desired level.

Hair Care Composition

A hair care composition in accordance with the present invention can be formulated to be a shampoo, a hair tonic, a setting lotion, a setting gel, a mousse, a hair spray, a conditioner, and a permanent or non-permanent hair color treatment, a permanent wave treatment, a hair relaxer treatment, and a pommade, for example. Preferably, a hair care composition includes a derivatized Arabinogalactan and a diluent suitable for application to the hair. "Suitable for application to the hair" means that the diluent does not negatively affect the aesthetics of hair (e.g., shine, managability, and the like) or cause irritation to the underlying skin. One with skill in the art will recognize that the appropriate choice of diluent will depend upon the form of delivery, for example, if the hair care composition is to be rinsed off after application (as is the case with shampoos, conditioners, and most hair color treatments) or left on the hair after application (as is the case with hair holding products, styling aids such as hair sprays and styling gels, mousses, and tonics).

Suitable diluents for application to the hair can include a wide range components conventionally used in hair care compositions. They can include water, an organic solvent, and a combination thereof. A suitable solvent is preferably selected from the group consisting of an alcohol, a hydrocarbon solvent, a halogenated hydrocarbon solvent (e.g., such as that commercially available under the trade designation FREON, from Dupont, Wilmington, Del.), an ester (e.g., ethyl acetate, dibutyl phthalate), a silicon-containing solvent, and a combination thereof. Preferably, an alcohol has from about 1 to about 6 carbon atoms, and can be selected from the group consisting of ethanol, isopropanol, and a combination thereof.

A suitable hydrocarbon solvent can be a linear or a branched chain hydrocarbon, preferably a saturated branched chain hydrocarbon. Preferably, preferred saturated branched hydrocarbons have from about 7 to about 14, more preferably from about 10 to about 13, and even more preferably from about 11 to about 12 carbon atoms, and can be selected from the group consisting of isobutane, hexane, heptane, octane, decene, and a combination thereof. Fatty alcohols are also useful, including stearyl and cetyl alcohols, as well as their ethoxylated and propoxylated derivatives, and a combination thereof.

Preferably, a silicone-containing solvent includes siloxanes, such as phenyl pentamethyl disiloxane, phenylethylpentamethyl disiloxane, hexamethyl disiloxane, methoxy propylemethyl cyclotetrasiloxane, chloropropyl pentamethyl disiloxane, hydroxypropyl pentamethyl disiloxane, octamethyl cyclotetrasiloxane, decamethyl cylcopentasiloxane, and a combination thereof.

In one embodiment, when the hair care composition is a hair holding composition, or a styling aid, such as a hair spray, mousse, gel, tonic, etc., the preferred solvents include water, ethanol, a silicone-containing solvent, and a combination thereof. Mousses and aerosol/atomized hair sprays preferably include a conventional propellant to deliver the composition as a foam (mousse) or as a fine, preferably uniform, spray (aerosol/atomized hair spray). Examples of propellants include difluoroethane, chlorodifluoroethane, dimethylether, propane, n-butane, isobutane, carbon dioxde, nitrogen, and compressed air. If included, a propellant is preferably present in a mousse in an amount of about 2% to about 30% by weight, and preferably present in an aerosol hair spray in an amount of about 15% to about 70% by weight.

A tonic or hair spray composition having a low viscosity can include an emulsifier, preferably selected from the group consisting of a nonionic surfactant, a cationic surfactant, an anionic surfactant, an amphoteric surfactant, and a combination thereof. In a hair spray composition, for example, an amphoteric surfactant can be used. If included, an emulsifier is preferably present in the hair care composition in an amount of about 0.01% to about 7.5% by weight of the composition.

In another embodiment, when the hair care composition is a shampoo, conditioner, and a combination thereof, it can include from about 9% to about 35% by weight anionic surfactant, from about 1% to about 20% by weight amphoteric surfactant (e.g., cocamidopropyl betaine), from about 1% to about 10% by weight of a conditioner and foam/lather modifier (such as an alkanolamide), from about 1% to about 10% by weight of a conditioner and foam/lather modifier (such as an amine oxide), from about 0.05% to about 1% by weight of a polymeric thickener, from about 0.05% to about 4% by weight of a thickener (e.g., an inorganic salt such as sodium chloride), from about 0.1% to about 1% by weight of an opacifier (e.g., glycol stearate), from about 0.05% to about 2% by weight fragrance, from about 0.0001% to about 0.01% by weight dye, from about 0.05% to about 5% by weight derivatized Arabinogalactan, and the remainder water. A suitable dye can be one or more of any number of the dyes referred to as "certified color," where the color identifier is typically prefaced by "FD&C" or "D&C."

In shampoo, for example, a lower formulation viscosity can be achieved at the higher polymer loading and substantivity (given the same D.S.) than can otherwise be achieved using conventional derivatized polymers. Higher solids and therefore higher charge and substantivity, at the same overall D.S., can be obtained through the use of higher amounts of derivatized Arabinogalactan in the formulation. Unexpectedly, the rheology or flow characteristics of these formulations can be improved by including derivatized Arabingalactan. It is believed that they are more Newtonian in their character and demonstrate reduced shear thinning, as compared to compositions including conventional derivatized polysaccharides. Further, the Arabinogalactan derivative has a higher solubility and therefore produces clearer solutions, at higher salt concentrations as compared with currently available polymer derivatives.

Skin Care/Cosmetic Compositions

A skin care/cosmetic composition in accordance with the present invention includes a derivatized Arabinogalactan in a cosmetically acceptable diluent. "Cosmetically acceptable" means that the diluent is suitable for application to the skin, has good aesthetic properties, is compatible with the derivatized Arabinogalactan and any other component of the composition, and does not irritate the skin upon application, preferably upon topical application. Preferably, a skin care/cosmetic composition in accordance with the present invention includes about 5% to about 99%, more preferably about 25% to about 99%, and even more preferably about 50% to about 97% by weight of the diluent.

Optional Additives

A personal care compositions in accordance with the present invention can include one or more optional additive. Preferred optional additives are selected from the group consisting of a specialized active ingredient, a conditioner, a humectant, a moisturizer, an emulsifier, an emollient, an antioxidants, a chelator, a preservative, an aesthetic agent, and a combination thereof. Aesthetic agents can be a fragrance, essential oils and extracts from plants, dyes, opacifiers, pearlizing agents, and the like.

Specialized Active Ingredients

A personal care composition can include an effective amount of a specialized active ingredient. "An effective amount" means that a specialized active ingredient is present in a personal care composition at a level that is high enough to positively modify the condition to be treated but is low enough to avoid negative effects, as can be determined by those of skill in the art or as described in an OTC Monograph issued by the FDA. For example, when the personal care composition is a skin care composition, one with skill in the art will recognize that an effective amount will vary depending upon the nature of the specialized active ingredient, the amount of composition to be applied to the skin, the particular condition to be treated, the age and physical condition of the user, the severity of the condition, the duration of the treatment, the nature of concurrent treatment, and other factors known in the art. In skin care compositions, a specialized active ingredient can be present in an amount of 0.01% to about 10%, preferably about 0.1% to about 5% of the composition. A combination of specialized active ingredients can be included in a personal care composition in accordance with the present invention.

For hair care compositions, a specialized active ingredient can be selected from the group consisting of an anti-dandruff agent (e.g., zinc pyrithione, octopirox, selenium disulfide, sulfur, coal tar, and the like), an anti-lice agent, a hair growth promoter, an anti-itch agent, and the like.

For cosmetic/skin care compositions, a specialized active ingredient can be selected from the group consisting of an anti-acne agent, a vitamin and derivative thereof, an analgesic agent, an exfoliant, a skin healant, an antipuritic agent (e.g., methdilizine and trimeprazine), an anesthetic agent, an antimicrobial agent (as described in U.S. Pat. No. 5,863,527 to Hutchins et al., including antibacterial, antifungal, antiprotozoan, and antiviral agents), a sunscreen agent, a skin lightening agent (e.g., hydroquinone, ascorbic acid, kojic acid, and sodium metabisulfate), an antiperspirant agent, and a combination thereof.

A suitable anti-acne agent can be selected from the group consisting of salicylic acid, sulfur, lactic acid, glycolic acid, pyruvic acid, urea, resorcinol, N-acetylcysteine, vitamins and derivatives thereof (including retinoic acid, e.g., cis- and trans-), antibiotic and antimicrobial agents (including benzoyl peroxide, octopirox, erythromycin, zinc, tetracyclin, triclosan, azelaic acid and its derivatives, phenoxy ethanol, phenoxy ethanol, ethylacetate, clindamycin, meclocycline), sebostats such as flavinoids, alpha and beta hydroxy acids, bile salts such as scymmol sulfate and its derivatives, deoxycholate, cholate, and a combination thereof.

A suitable analgesic agent can be selected from the group consisting of salicylic acid and derivatives thereof (e.g., methyl salicylate), capsicum and derivatives thereof (e.g., capsaicin), and non-steroidal anti-inflammatory drugs such as propionic acid derivatives, acetic acid derivatives, fenamic acid derivatives, biphenylcarboxylic acid derivatives, and oxicams, all as described in U.S. Pat. No. 4,985,459 to Sunshine et al.), steroidal anti-inflammatory agents (e.g., hydrocortisone), and a combination thereof.

A suitable sunscreen agent can be selected from the group consisting of 2-ethylhexyl p-methoxycinnamate, 2-ethylehexyl N,N-dimethyl-p-aminobenzoate, p-aminobenzoic acid, 2-phenylbenzimidazole-5-sulfonic acid, octocrylene, oxybenzone, homomethyl salicylate, octyl salicylate, 4,4'-methoxy-t-butyldibenzoylmethane, 4-isopropyl dibenzoylmethane, 3-benzylidene camphor, 3-(4-methylbenzylidene) camphor, titanium dioxide, zinc oxide, silica, iron oxide, and mixtures thereof. Other suitable sunscreen agents that can be generally categorized as a single molecule having two chromophore moieties that exhibit different ultra-violet radiation adsorption spectra. Preferably, one chromophore absorbs predominately in the UVB radiation range while another chromophore absorbs predominately in the UVA radiation range. Examples of this type of sunscreen agent include 4-N,N-(2-ethylhexyl) methylaminobenzoic acid ester of 2,4-dihydroxybenzophenone, 4-N,N-(2-ethylhexyl) methylaminobenzoic acid ester with 4-hydroxydibenzoylmethane, 4-N,N-(2-ethylhexyl)methylaminobenzoic acid ester of 2-hydroxy-4-(2-hydroxyethoxy)benzophenone, 4-N,N-(2-ethylhexyl) methylaminobenzoic acid ester of 4-(2-hydroxyethoxy)dibenzoylmethane, and a combination thereof.

In a personal care composition in accordance with the present invention, a sunscreen agent can be present in an amount of about 0.5% to about 20% of the composition. Exact amounts of a sunscreen agent will depend upon the nature of the agent used and the desired Sun Protection Factor (SPF) that is commonly used as a measure of photoprotection of a sunscreen agent against erythema.

A self-tanning agent can also be included and can be one or more of a number of conventional agents including dihydroxyacetone, glyceraldehyde, indoles and their derivatives, and the like.

Antiperspirant agents include astringent metallic compounds, particularly inorganic and organic salts of aluminum, zirconium, zinc, and a combination thereof. For example, the antiperspirant agent can be selected from the group of aluminum halides, aluminum hydroxy halides, zirconyl oxide halides, zirconyl hydroxy halides, and a combination thereof.

A deodorant is typically in the form of a bacteriostat and can be included in a personal care composition of the present invention, particularly a skin care composition. Suitable deodorants are described in U.S. Pat. No. 5,863,527 to Hutchins et al., and include zinc phenolsulfonate, 2,4,4'-trichloro-2'-hydroxy (diphenyl ether), N-lauroyl sarcosine, sodium N-palmitoyl sacrosine, for example.

Conditioner

A personal care composition, preferably a hair care composition, in accordance with the present invention can include a conditioner. Conditioners particularly useful for hair care compositions include quaternary ammonium compounds, silicone conditioning agents, fatty alcohols, amine oxides, alkanolamides, and the like. Silicones include cyclic or linear polydimethylsiloxanes, phenyl and alkyl phenyl silicones, and silicone copolyols.

Method of Using Personal Care Compositions

A personal care composition in accordance with the present invention can be used in conventional methods to provide the desired benefit from the appropriate composition. For example, a desired benefit from a hair care composition can include styling, holding, conditioning, cleansing, coloring, perming, straightening, and a combination thereof. A desired benefit from a cosmetic/skin care composition can include cleansing, moisturizing, sun protection, acne treatment, exfoliation, wrinkle treatment, artificial tanning, and a combination of these and other cosmetic and pharmaceutical benefits.

Methods of use depend on the type of composition employed but generally involved application of an effective amount of the composition to the hair or skin, which may then be rinsed from the hair or skin, in the case of some shampoos/conditioners and skin cleansers. Alternatively, after the composition is applied, it may be allowed to remain on the hair (as in the case of a hair spray, a mousse, a styling gel, and a leave-in conditioner) or on the skin (in the case of moisturizing creams and lotions, and many treatment creams and lotions for acne, wrinkles, exfoliation, self-tanning, and the like). "An effective amount" means that portion of the composition required for the desired result.

Preferably, for a hair rinse, mousse, and gel, the composition is applied to wet or damp hair prior to drying and styling of the hair. Hair sprays are typically applied to dry hair after styling. Cosmetic and skin care compositions are typically applied to and rubbed into the skin, that can be wet, damp, or dry.

EXAMPLES

The following non-limiting examples will further illustrate the invention. All parts, percentages, ratios, etc., in the examples are by weight/weight % unless otherwise indicated.

The viscosity impact of a derivatized Arabinogalactan was evaluated as compared to other polymers. The following table summarizes that the polymers that were evaluated.

TABLE 1

| Example | Commercial Designation | Compound |
|---|---|---|
| Example 1 | LARACARE C300, from Larex, Inc., St. Paul, MN | Quaternized Arabinogalactan |
| Comparative Example A | LARACARE A200, from Larex, Inc., St. Paul, MN | Arabinogalactan (underivatized) |
| Comparative Example B | UCARE POLYMER JR 125, from Amerchol Corp., Edison, NJ | Polyquaternium-10 (derivatized hydroxyethyl cellulose) |
| Comparative Example C | MERQUAT 550, from Calgon Corp., Pittsburgh, PA | Polyquaternium-7 (derivatized acrylamide) |
| Comparative Example D | JAGUAR C-14S, from Rhone-Poulenc, Cranbury, NJ | Hydroxypropyl quar hydroxypropyltrimonium chloride |
| Comparative Example E | JAGUAR C-162, from Rhone-Poulenc, Cranbury, NJ | Hydroxypropl quar hydroxypropyltrimonium chloride |

A solution using deionized water was prepared using each polymer above at various concentrations. It was noted that Example 1 and Comparative Example A were easily dissolved at the various concentrations. Comparative Example B required about 30 minutes before substantially homogeneous solutions were obtained. Because Comparative Example C was supplied in a liquid form, it readily formed substantially homogeneous solutions. A pH adjustment to solutions containing Comparative Examples D and E was required before substantially homogeneous solutions were obtained. A 3N HCl solution was used to adjust the pH within a range from about 5 to about 6.

Viscosity for each of the solutions was measured at ambient temperature using a Brookfield Viscometer model LVTCP (from Brookfield Engineering Laboratories, Inc., Stoughton, Mass.) having an approximate upper limit of about 1000 cps. The following table summarizes the viscosity measurements for various concentrations of the polymers.

TABLE 2

| Viscosity Measurements (cps) | | | | | | |
|---|---|---|---|---|---|---|
| Concentration (w/w %) | Ex. 1 | Comp. Ex. A | Comp. Ex. B | Comp. Ex. C | Comp. Ex. D | Comp. Ex. E |
| 0.25 | N/D | N/D | N/D | N/D | 77.6 | 13.0 |
| 0.5 | N/D | N/D | N/D | 7.55 | 785 | 42.65 |
| 1.0 | 1.002 | 1.027 | 2.94 | 17.0 | * | 564.5 |
| 2.0 | 1.053 | 1.074 | 4.236 | 1120 | * | * |
| 5.0 | 1.202 | 1.268 | 7.548 | * | * | * |
| 10.0 | 1.56 | 1.715 | 12.415 | * | * | * |

TABLE 2-continued

Viscosity Measurements (cps)

| Concentration (w/w %) | Ex. 1 | Comp. Ex. A | Comp. Ex. B | Comp. Ex. C | Comp. Ex. D | Comp. Ex. E |
|---|---|---|---|---|---|---|
| 25.0 | 4.89 | 5.1 | 67.25 | * | * | * |
| 50.0 | 112.13 | 100.08 | 655 | * | * | * |

"N/D" indicates that viscosity measurements were not taken.
"*" indicates that the viscosity was greater than the approximate upper limit of the viscometer and could not be measured.

Figure 7:
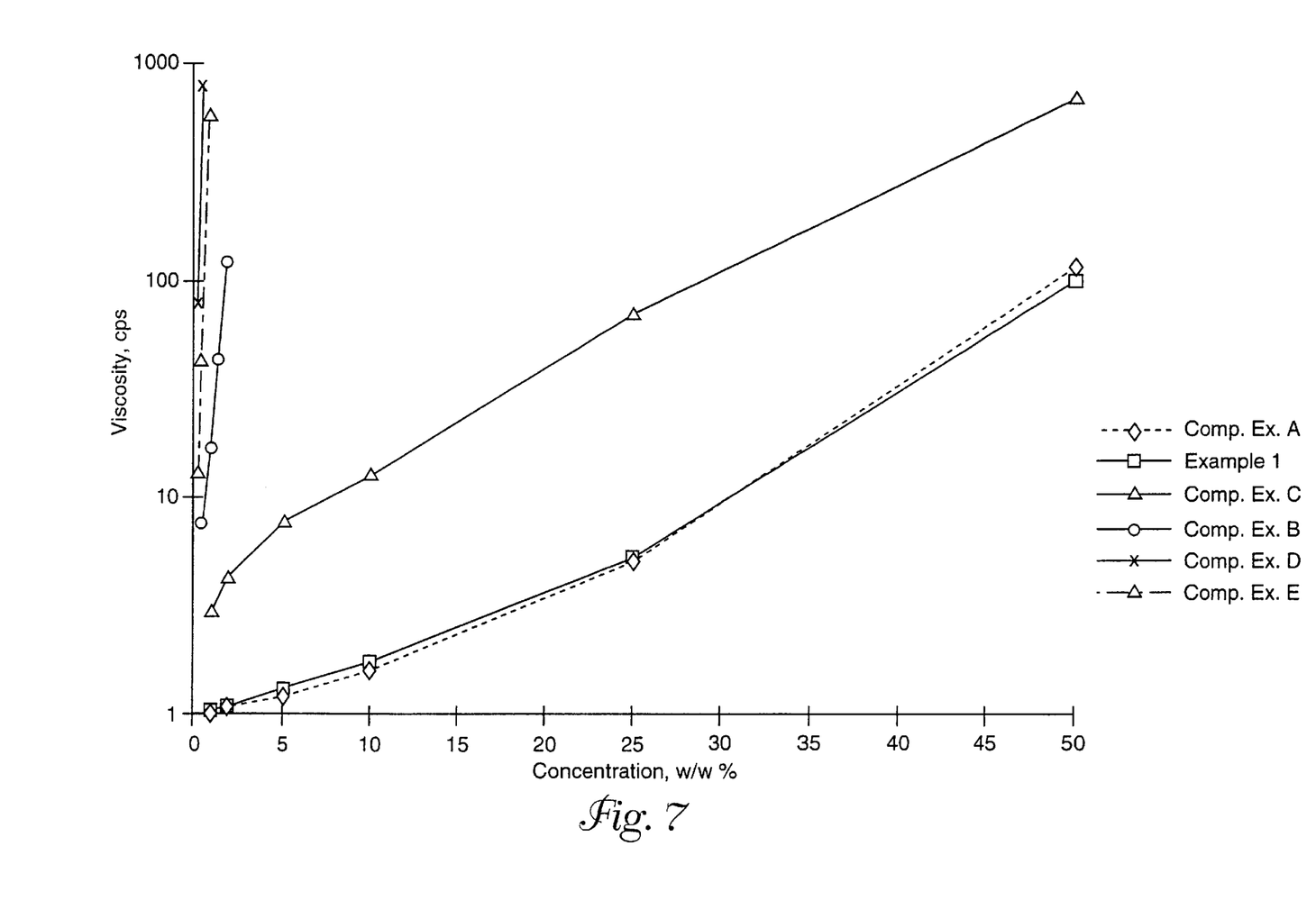
FIG. 7 illustrates the impact on viscosity of aqueous solutions of a derivatized Arabinogalactan as compared to other polymers.

The data above (that has also been graphed as shown in FIG. 7), illustrated that derivatized Arabinogalactan had a significantly less impact on the viscosity of a solution at various concentrations, as compared to other derivatized polymers. See, Example 1 versus Comparative Examples B–E. Further, the derivatized Arabinogalactan exhibited a similar effect on the viscosity as underivatized Arabinogalactan for similar concentrations. See, Example 1 as compared to Comparative Example A. Thus, it is believed that the amount of derivatized Arabinogalactan can be varied within a fairly wide concentration range, depending upon the results it is desired to deliver, in a particular composition without significantly adversely impacting the overall viscosity of the composition.

Patents and patent applications disclosed herein are hereby incorporated by reference as if individually incorporated. It is to be understood that the above description is intended to be illustrative, and not restrictive. Various modifications and alterations of this invention will become apparent to those skilled in the art from the foregoing description without departing from the scope and the spirit of this invention, and it should be understood that this invention is not to be unduly limited to the illustrative embodiments set forth herein.

What is claimed is:

1. A personal care composition comprising a derivatized Arabinogalactan comprising at least one cationic moiety wherein the personal care composition is selected from the group consisting of a hair care composition, a skin care composition, a cosmetic, and a fragrance composition.

2. The composition of claim 1, wherein the derivatized Arabinogalactan is selected from the group consisting of a single derivatized Arabinogalactan, a double derivatized Arabinogalactan, and a combination thereof.

3. The composition of claim 1, wherein the derivatized Arabinogalactan is selected from the group consisting of hydroxypropyl Arabinogalactan, carboxymethyl hydroxypropyl Arabinogalactan, quaternary ammonium Arabinogalactan, carboxymethyl Arabinogalactan, and a combination thereof.

4. The composition of claim 1, wherein the personal care composition is a skin care composition.

5. The composition of claim 1, wherein the derivatized Arabinogalactan is derivatized with a derivatizing reagent that is present in an amount from about 1% to about 200% of a weight of Arabinogalactan.

6. A personal care composition comprising a diluent and derivatized Arabinogalactan comprising at least one cationic moiety, the derivatized Arabinogalactan produced by combining Arabinogalactan with a derivatizing reagent selected from the group consisting of ethylene oxide, propylene oxide, a quaternary amine, sodium monochloroacetate, dimethylsulfate, methyl chloride, ketene, vinyl acetate, and a combination thereof.

7. The personal care composition of claim 6, wherein the derivatized Arabinogalactan is selected from the group consisting of a single derivative of Arabinogalactan, a double derivative of Arabinogalactan, and a combination thereof.

8. The personal care composition of claim 6, wherein the derivatized Arabinogalactan is selected from the group consisting of hydroxypropyl Arabinogalactan, carboxymethyl hydroxypropyl Arabinogalactan, quaternary ammonium Arabinogalactan, carboxymethyl Arabinogalactan, and a combination thereof.

9. The personal care composition of claim 6, comprising from about 0.05% to about 25% by weight derivatized Arabinogalactan.

10. The personal care composition of claim 6, further comprising at least one additive selected from the group consisting of a surfactant, an emulsifier, a foam modifier, a humectant, a moisturizer, a thickener, an emollient, a conditioning agent, a specialized functional ingredient, a preservative, an antioxidant, a chelator, a sequestrant, and an aesthetic component.

11. The personal care composition of claim 6, wherein the derivatized Arabinogalactan is quaternized ammonium Arabinogalactan.

12. The personal care composition of claim 11, wherein the personal care composition is a hair care composition.

13. The personal care composition of claim 12, wherein the hair care composition is selected from the group consisting of a shampoo, a conditioner, a hair tonic, a setting lotion, a setting gel, a mousse, a hair spray, a permanent hair color treatment, a non-permanent hair color treatment, a permanent wave treatment, a hair relaxer, and a pomade.

14. The personal care composition of claim 6, further comprising a specialized active ingredient in an amount of about 0.01% to about 10% by weight of the composition.

* * * * *

UNITED STATES PATENT AND TRADEMARK OFFICE
CERTIFICATE OF CORRECTION

PATENT NO. : 6,290,978 B2
DATED : September 18, 2001
INVENTOR(S) : Mak et al.

It is certified that error appears in the above-identified patent and that said Letters Patent is hereby corrected as shown below:

<u>Title page,</u>
Item [73], Assignee, please delete "White Bear Lake, MI" and insert -- White Bear Lake, Minnesota -- therefor.
Item [56], FOREIGN PATENT DOCUMENTS, please insert -- 633964 11/1978 (SU) --.

<u>Column 1,</u>
Line 1, please delete "." which occurs after the word "OF".

<u>Column 2,</u>
Line 12, please delete "cxaiiplc" and insert -- example -- therefor.
Line 13, please delete "thcsc" and insert -- these -- therefor.
Line 47, please delete "comparability" and insert -- compatability -- therefor.

<u>Column 3,</u>
Line 24, please delete "Larix" and insert -- *Larix* -- therefor.

<u>Column 5,</u>
Line 24, please delete "Larix" and insert -- *Larix* -- therefor.
Line 25, please delete "Arabinogalaetan" and insert -- Arabinogalactan -- therefor.

<u>Column 10,</u>
Line 39, please delete "formns" and insert -- forms -- therefor.

<u>Column 11,</u>
Line 46, please delete "quatemary" and insert -- quaternary -- therefor.

<u>Column 15,</u>
Line 58, please delete "effectivc" and insert -- effective -- therefor.

UNITED STATES PATENT AND TRADEMARK OFFICE
CERTIFICATE OF CORRECTION

PATENT NO. : 6,290,978 B2
DATED : September 18, 2001
INVENTOR(S) : Mak et al.

It is certified that error appears in the above-identified patent and that said Letters Patent is hereby corrected as shown below:

Column 16,
Line 42, please insert -- ( -- before the word "such".

Signed and Sealed this

First Day of April, 2003

JAMES E. ROGAN
*Director of the United States Patent and Trademark Office*